United States Patent [19]

Liao et al.

[11] Patent Number: 5,300,591
[45] Date of Patent: Apr. 5, 1994

[54] BLENDS CONTAINING CYANATE-SILOXANES

[75] Inventors: Zeng K. Liao, Lake Jackson, Tex.; Chun S. Wang, Tainan, Taiwan

[73] Assignee: The Dow Chemical Company, Midland, Mich.

[21] Appl. No.: 93,497

[22] Filed: Jul. 16, 1993

Related U.S. Application Data

[60] Division of Ser. No. 837,464, Feb. 14, 1992, Pat. No. 5,260,398, which is a continuation-in-part of Ser. No. 505,310, Apr. 5, 1990, abandoned.

[51] Int. Cl.$^5$ .................. C08F 283/00; C08F 283/12; C08G 77/00; C08L 83/00
[52] U.S. Cl. ...................... 525/474; 528/15; 528/19; 528/18; 528/21; 528/28; 528/26; 528/32
[58] Field of Search ........ 528/15, 19, 18, 21, 528/28, 26, 32; 525/474

[56] References Cited

U.S. PATENT DOCUMENTS

| | | | |
|---|---|---|---|
| 3,448,079 | 6/1969 | Grigat et al. | 260/59 |
| 3,658,623 | 4/1972 | Grigat et al. | 156/331 |
| 3,896,123 | 7/1975 | DeZuba et al. | 528/28 |
| 4,070,416 | 1/1978 | Narahara et al. | 260/830 P |
| 4,097,455 | 6/1978 | Burkhardt et al. | 260/47 C B |
| 4,206,299 | 6/1980 | Yamazaki et al. | 528/28 |
| 4,590,224 | 5/1986 | Frisch, Jr. | 521/155 |
| 4,608,434 | 8/1986 | Shimp | 528/422 |
| 4,665,154 | 5/1987 | Varnell et al. | 528/205 |
| 4,707,529 | 11/1987 | Hoffman et al. | 525/476 |
| 4,748,270 | 5/1988 | Murray et al. | 560/301 |
| 4,751,323 | 6/1988 | Woo et al. | 560/301 |
| 4,777,226 | 10/1988 | Holte | 525/534 |
| 4,782,178 | 11/1988 | Godschalx | 560/301 |
| 4,785,075 | 11/1988 | Shimp | 528/422 |
| 4,797,454 | 1/1989 | Ryang | 528/28 |

FOREIGN PATENT DOCUMENTS 0258695 3/1988 European Pat. Off. .
0269412 6/1988 European Pat. Off. .

OTHER PUBLICATIONS

"Novel Synthetic Methods for Condensation Polymers Using Silylated Nucleophilic Monomers" by Yoshio Imai and Yoshiyuki Oishi, Prog. Polym. Sci., vol. 14, 173-193, 1989, Pergamon Press.

Primary Examiner—Melvyn I. Marquis
Assistant Examiner—Karen A. Dean

[57] ABSTRACT

Blends containing (1) at least one compound containing an average of more than one vicinal aromatic cyanate group per molecule and at least one organosiloxane moiety per molecule and (2) at least one compound containing an average of more than one vicinal aromatic cyanate group per molecule which is substantially free of organosiloxane moieties. The compositions are useful as a component in adhesives, coatings, laminates, composites, encapsulants, filament winding, and molding.

5 Claims, No Drawings

BLENDS CONTAINING CYANATE-SILOXANES

CROSS-REFERENCE TO RELATED APPLICATION

This application is a division of application Ser. No. 07/837,464 filed Feb. 14, 1992 now U.S. Pat. No. 5,260,398 which is a continuation-in-part of application Ser. No. 07/505,310 filed Apr. 5, 1990 now abandoned which are incorporated herein in their entirety.

FIELD OF THE INVENTION

The present invention pertains to aromatic cyanate-containing compounds with organosiloxane moieties and curable and cured products thereof.

BACKGROUND OF THE INVENTION

Aromatic cyanate-containing compounds are disclosed in U.S. Pat. Nos. 4,748,270; 4,751,323; 4,754,213; 4,608,434; 4,070,416; 4,097,455; and 3,562,214. These thermally reactive esters can undergo crosslinking via trimerization in the presence of catalysts and the cured (thermoset) resins have useful properties, such as high glass transition temperatures; low dielectric constants; and thermal stability. While the resultant products possess good properties, it is always desirable to have available products with improved properties. It would therefore be desirable to have cured products which possess an improvement in one or more of the desirable properties such as, for example, thermal stability, moisture resistance, electrical properties, low stress and the like. U.S. Pat. No. 4,797,454 issued Jan. 10, 1989 discloses bifunctional cyanate-oxazolinyl-group containing siloxanes reaction product from cyanate ester and epoxysiloxane.

SUMMARY OF THE INVENTION

One aspect of the present invention pertains to compounds containing an average of more than one aromatic cyanate group and at least one organosiloxane moiety per molecule represented by the following general formulas I, II, III, or IV

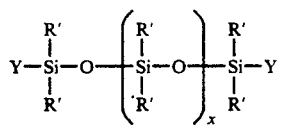

Formula I

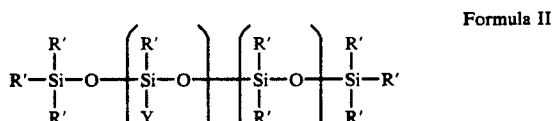

Formula II

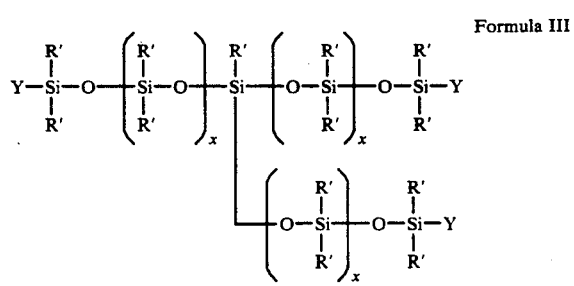

Formula III

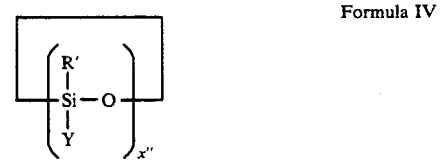

Formula IV wherein each R' is independently a hydrocarbyl group having suitably from 1 to about 20 carbon atoms; each Y is a hydrocarbyl group having from 2 to about 20 carbon atoms or an entity represented by the following formulas V, VI, VII, VIII, IX, X, or XI with the proviso that at least an average of more than one Y is other than a hydrocarbyl group:

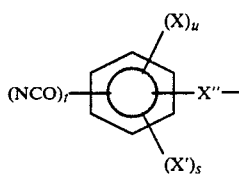

Formula V

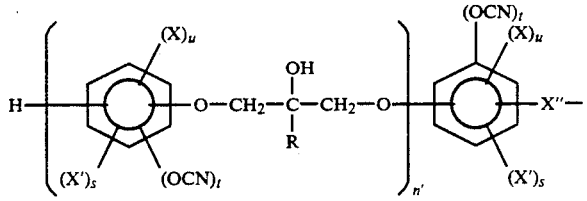

Formula VI

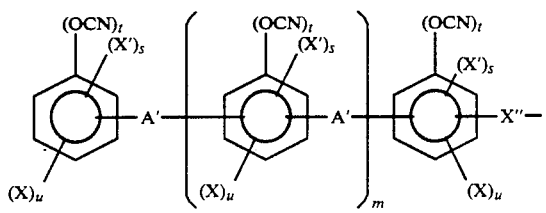

Formula VII

-continued

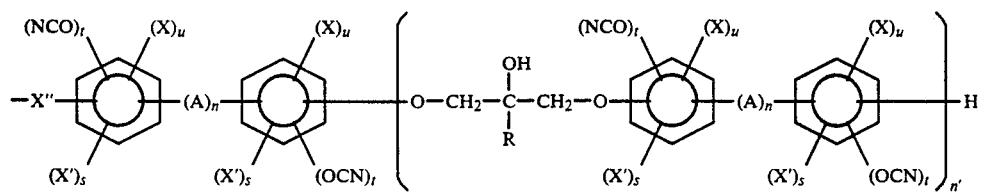

Formula VIII

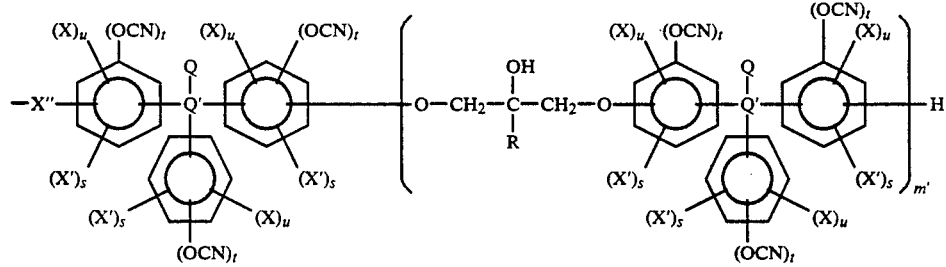

Formula IX

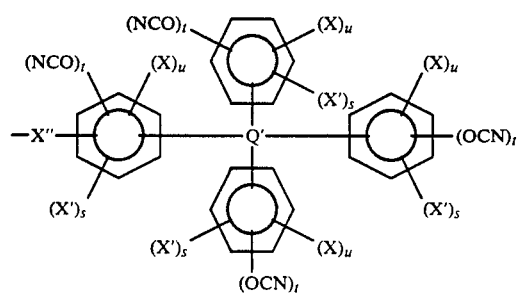

Formula X

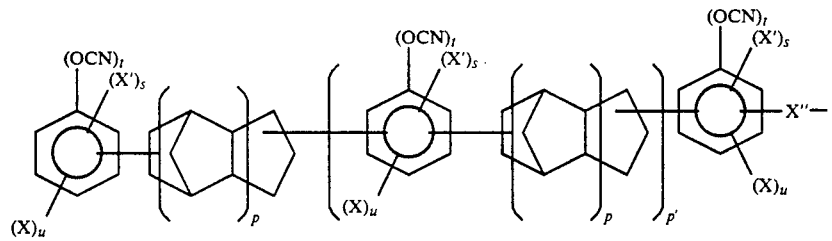

Formula XI wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom, or a hydroxyl group; each X' is independently hydrogen or an unsaturated aliphatic or unsaturated cycloaliphatic group or such unsaturated aliphatic or unsaturated cycloaliphatic group having an oxygen atom between such group and the aromatic ring, such as, for example, —CH$_2$— CH=CH$_2$, —CH=CH$_2$, —O—CH$_2$—CH=CH$_2$, cyclohexenyl, bicyclo(2.2.1)hept-1-yl, vinyl benzyl ether or the like; each X" is independently a divalent aliphatic or a divalent cycloaliphatic group; each m independently has an average value from about 0.01 to about 8; each m' independently has an average value from about zero to about 8; each n independently has a value of zero or 1; each n' independently has an average value from about 0.001 to about 20; each n$^1$ independently has a value from 1 to about 3; each p independently has a value from zero to about 10; each p' independently has an average value from zero to about 8; and each s, t and u independently has a value from 1 to about 3 with the proviso that the sum of s, t and u satisfies the valency of the ring; each x independently has a value from zero to about 500; each x' independently has a value from 2 to about 500; each x" independently has a value from 2 to about 10; and the sum of x and x' is from about 2 to about 1000.

Another aspect of the present invention pertains to a blend comprising (1) at least one compound having an average of more than one aromatic cyanate group and at least one organosiloxane moiety per molecule and (2) at least one compound having an average of more than one aromatic cyanate group per molecule which is substantially free of organosiloxane moieties.

Another aspect of the present invention pertains to a curable composition comprising (A) at least one compound containing an average of more than one aromatic cyanate group per molecule which comprises (1) from about 1 to about 100 percent by weight based upon the combined weight of components (1) and (2) of a compound having an average of more than one aromatic cyanate group and at least one organosiloxane moiety per molecule and (2) from about zero to about 99 percent by weight based upon the combined weight of components (1) and (2) of a compound having an average of more than one aromatic cyanate group per molecule which is substantially free of organosiloxane moieties; and (B) a curing amount of at least one curing catalyst therefor.

Another aspect of the present invention pertains to the product resulting from curing the aforementioned curable compositions.

The present invention incorporates an organosiloxane moiety into the cyanate-containing skeleton so as to modify these thermosetting resins. The cured resins are useful for electronic, coatings and composite applications and possess an improvement in one or more of the properties such as, for example, thermal stability, moisture resistance, electrical properties, low stress and the like.

DETAILED DESCRIPTION OF THE INVENTION

For purposes of the present invention, the term "aromatic" includes not only the pure aromatic ring compounds containing only carbon atoms in the ring structure, but also the heterocyclic rings containing carbon and sulfur, oxygen or nitrogen atoms in the ring structure.

The cyanate-containing compounds of the present invention which contain organosiloxane moieties can be prepared by reacting aromatic hydroxyl-containing compounds having one or more organosiloxane moieties in their backbone with cyanogen halide or in situ formed cyanogen halide in the presence of a base as a catalyst. The reaction is conducted at a temperature suitably from about −60° C. to about 60° C., preferably from about −40° C. to about 40° C., more preferably form about −20° C. to about 20° C. for a time sufficient to complete the reaction, usually from about 0.2 to about 10, preferably from about 0.3 to about 8, more preferably from about 0.5 to about 4, hours. If desired, the reaction can be conducted in the presence of a suitable solvent such as, for example, aromatic hydrocarbons, halogenated aliphatic hydrocarbons, cyclic ethers, nitriles, glycol ethers and the like. Suitable such solvents include, for example, methylene chloride, dioxane, acetonitrile, toluene, dimethoxy diglycol ether, combinations thereof and the like. A particularly suitable solvent is methylene chloride.

Suitable basic catalysts which can be employed in the preparation of the cyanate-containing compounds of the present invention include, for example, tertiary amines such as, for example, triethyl amine, tributyl amine, trioctyl amine, combinations thereof and the like. The preferred catalyst is triethylamine. This method is more fully described in U.S. Pat. No. 4,748,270 which is incorporated herein by reference in its entirety.

The compounds containing aromatic hydroxyl groups and organosiloxane moiety(ies) which can be employed herein to react with the cyanogen halide so as to prepare the cyanate-containing compounds of the present invention can be prepared by the hydrosilylation method which comprises reacting in the presence of a suitable catalyst, with or without a solvent, an aromatic hydroxyl-containing compound containing aliphatic or cycloaliphatic double bonds with an organohydrosiloxane compound as described by John L. Speier in Advances in Organometallic Chemistry, vol. 17, Academic Press, Inc., pp 407–447, 1979 which is incorporated herein by reference in its entirety. The reaction is usually conducted at temperatures of from about 10° C. to about 150° C., preferably from about 30° C. to about 120° C., more preferably from about 40° C. to about 100° C. Finally, the excessive unreacted ≡Si—H bonds are terminated, quenched, by addition of a mono- or di-unsaturated aliphatic or cycloaliphatic alkene having from about 4 to about 20, preferably from about 6 to about 16, more preferably from about 7 to about 12, carbon atoms such as, for example, noborylene, n-octene, cyclohexene, dicyclopentadiene, and the like.

Suitable aromatic hydroxyl-containing compounds which can be employed in this method to prepare the aromatic hydroxyl-containing compounds which also contain organosiloxane moiety(ies) employed to prepare the cyanate-containing compounds of the present invention include any compound containing at least one aromatic hydroxyl group per molecule and at least one aliphatic or cycloaliphatic double bond. Such compounds include, but are not limited to those compounds represented by the following general formulas XII, XIII, XIV, XV, XVI, XVII or XVIII

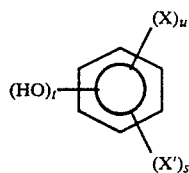

Formula XII

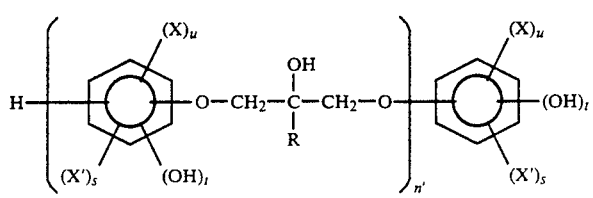

Formula XIII

-continued

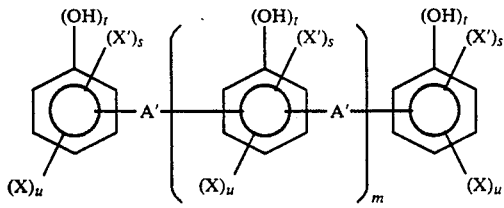
Formula XIV

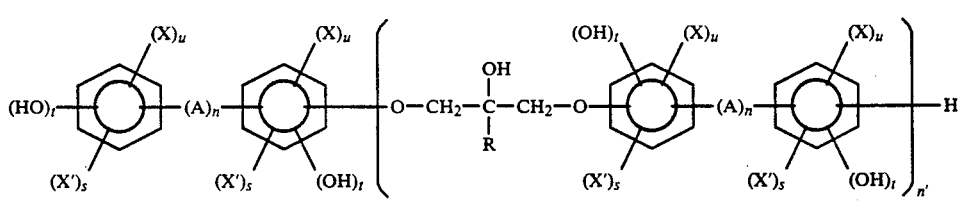
Formula XV

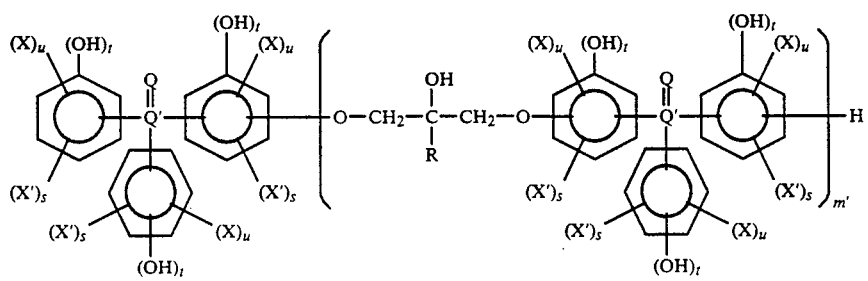
Formula XVI

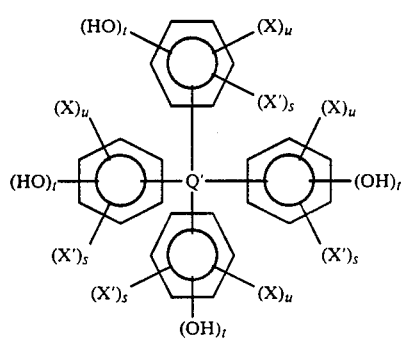
Formula XVII

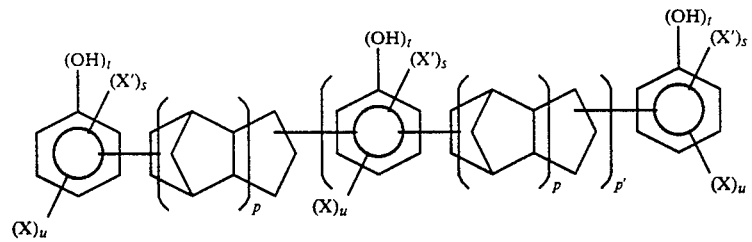
Formula XVIII wherein each A is independently a divalent hydrocarbyl group having suitably from 1 to about 20, more suitably from 1 to about 15, most suitably from 1 to about 10, carbon atoms, —O—, —S—, —S—S—, —SO—, —SO$_2$—, or —CO—; each A' is independently a divalent hydrocarbyl group having from 1 to about 20, more suitably from 1 to about 10, most suitably from 1 to about 2, carbon atoms; each Q is independently hydrogen or an alkyl group having from 1 to about 10 carbon atoms; each Q' is independently a tetravalent hydrocarbyl group having suitably from 1 to about 20, more suitably from 1 to about 10, most suitably from 1 to about 4, carbon atoms; each R is independently hydrogen or an alkyl group having from 1 to about 3 carbon atoms; each X is independently hydrogen, a hydrocarbyl or hydrocarbyloxy group having suitably from 1 to about 12, more suitably from 1 to about 6, most suitably from 1 to about 4, carbon atoms or a halogen atom, preferably bromine; each X' is independently hydrogen or an unsaturated aliphatic or unsaturated cycloaliphatic group or such unsaturated aliphatic or unsaturated cycloaliphatic group having an oxygen atom between such group and the aromatic ring, such as, for example, —CH$_2$—CH=CH$_2$, —CH=CH$_2$, —O—CH$_2$— CH=CH$_2$, cyclohexenyl, bicyclo-(2.2.1)hept-1-yl, vinyl benzyl ether or the like with the proviso that at least one of such groups is other than hydrogen; m has an average value suitably from about 0.01 to about 8, more suitably from about 1 to about 6, most suitably from about 2 to about 4; m' suitably has an average value from about zero to about 8, more suitably form about 1 to about 6, most suitably from about 2 to about 4; n has a value of zero or 1; n' suitably has an average value suitably from about 0.001 to about 20, more suitably from about 0.01 to about 12, most suitably from about 0.03 to about 5; each p suitably has a value from zero to about 10, more suitably from about 1 to about 5, most suitably from about 1 to about 3; each p' suitably has an average value from zero to about 8, more suitably from about 1 to about 6, most suitably from about 2 to about 4; and each s, u and t independently has a value from 1 to about 3 with the proviso that the sum of s, u and t satisfies the valency of the ring.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic groups can be saturated or unsaturated. Likewise, the term hydrocarbyloxy means a hydrocarbyl group having an oxygen linkage between it and the carbon atom to which it is attached.

Particularly suitable phenolic hydroxyl-containing compounds include, for example, 2-allylphenol; 4-hydroxyvinylbenzene (or 4-hydroxystyrene); 3,3'-diallylbisphenol-A; 3-monoallylbisphenol-A; 4-monoallylether bisphenol-A; 4,4'-bisallylethers bisphenol-A; cyclohex-1-ylmethylene diphenol or bicyclo(2.2.1)-hept-1-yl methylene diphenol; 3,3'-diallyl-4,4'-dihydroxydiphenol; 3,3'-diallyl-4,4'-dihydroxyphenyl methane; 4-allyl-2-methoxyphenol; also included are mono- or di-allyl ether of o-cresol-formaldehyde novolac; or phenol-formaldehyde novolac; or any combination thereof and the like.

Suitable hydrosiloxane compounds which can be employed to prepare the compounds containing aromatic hydroxyl groups and organosiloxane moieties include, for example, those represented by the following formulas XIX, XX, XXI, or XXII

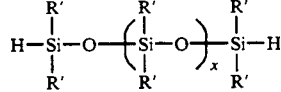

Formula XIX

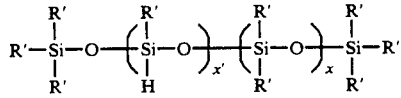

Formula XX

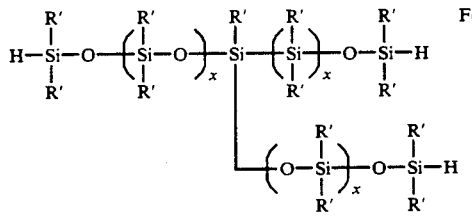

Formula XXI

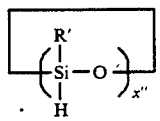

Formula XXII wherein each R' is independently a hydrocarbyl group having suitably from 1 to about 20, more suitably from 1 to about 10, most suitably from 1 to about 4, carbon atoms; each x independently has a value suitably from zero to about 500, more suitably from zero to about 250, most suitably from zero to about 125; each x' independently has a value suitably from 2 to about 500, more suitably from 2 to about 250, most suitably from 2 to about 125; x" has a value suitably from 2 to about 10, more suitably from about 3 to about 8, most suitably from about 4 to about 6; and the sum of x and x' is suitably from about 2 to about 1000, more suitably from about 2 to about 500, most suitably from about 2 to about 250.

Particularly suitably organohydrosiloxane compounds which can be employed include, for example, 1,1,3,3-tetramethyldisiloxane; 1,1,3,3,5,5-hexamethyltrisiloxane; 1,1,3,3,,5,,5,7,7-octamethyltetrasiloxane; 1,3-diphenyl-1,3-dimethyldisiloxane; 1,1,3,3-tetraisopropyldisiloxane; 1,3-diphenyl-1,1,3,3-tetrakis-(dimethylsiloxy)-disiloxane; 1,3,5,7-tetramethylcyclotetrasiloxane; 1,3,5,7,9-pentamethylcyclotetrasiloxane; 1,1,3,3-tetrakis-(trimethylsiloxy)-disiloxane; polymethylhydrosiloxane(M. W.=300–50,000); methylhydrodimethylsiloxane copolymer(M. W.=120–100,000); dimethylterminated-methylhydro-phenylmethylsiloxane copolymer (M. W.=120–100,000); combinations thereof and the like.

Suitable solvents or reaction medium which can be employed herein include, for example, aliphatic, cycloaliphatic or aromatic hydrocarbons such as, for example, n-hexane, cyclohexane, octane, toluene, xylene, any combination thereof and the like.

Suitable hydrosilylation catalysts which can be employed include the homogeneous catalysts which are disclosed by John L. Speier in *Advanced In Organometallic Chemistry*, Vol. 17, 407–447, by Academic Press Inc. (1979) which is incorporated herein by reference. Particularly suitable catalysts include, for example, chloroplatinic acid ($H_2PtCl_6$), as well as (($C_2H_4$)PtCl$_2$)$_2$, (bis-(triphenylphosphine)cobalt chloroiridium) (IrClCo(PPh$_3$)$_2$), dicobalt octacarbonyl (Co$_2$(CO)$_8$). Also, 10% Pd/C or 5% Pt/C and Raney Ni are effective catalysts for this reaction. Hydrosilylation catalysts which can be used also include those disclosed in U.S. Pat. Nos. 3,775,442, 3,159,601, 3,220,972, all of which are incorporated herein by reference. An effective amount of a platinum catalyst is from about 0.0005 to 1.05 percent by weight of platinum based on the weight of the hydrosilylation mixture.

A second method for preparing the compound containing aromatic hydroxyl groups and also containing organosiloxane moieties, which can be employed herein to react with the cyanogen halide so as to prepare the cyanate-containing compounds of the present invention, is by reacting an aromatic hydroxyl-containing compound having one or more aromatic or heterocyclic rings and at least one ortho or para position relative to an aromatic hydroxyl group available for ring alkylation with a di-or multi-unsaturated aliphatic or cycloaliphatic hydrocarbon containing an organosiloxane moiety in its backbone in the presence of a catalyst and in the presence or absence of a solvent or inert reaction medium such as, for example chlorobenzene. This method is described by Donald L. Nelson in U.S. Pat. No. 4,390,680 and by Paul G. Schrader in U.S. Pat. No. 4,394,496, both of which are incorporated herein by reference in their entirety. Particularly suitable catalysts include, for example, Lewis acids such as, for example, HCl, $H_2SO_4$, $BF_3$.etherate, TiCl$_4$, ZrCl$_4$, CH$_3$SO$_3$H, p-toluene sulfonic acid, oxalic acid, combinations thereof and the like.

Suitable aromatic hydroxyl-containing compounds which can be employed to prepare the compounds containing aromatic hydroxyl groups and also containing organosiloxane moieties by this second method include the previously mentioned compounds represented by formulas XII, XIII, XIV, XV, XVI, XVII or XVIII except that each X' is independently hydrogen, a hydrocarbyl or hydrocarbyloxy group having suitably from 1 to about 12, more suitably from 1 to about 6, most suitably from 1 to about 4, carbon atoms or a halogen atom, preferably bromine. Also suitable are the heterocyclic compounds containing an aromatic hydroxyl group such as, for example, those represented by the following general formulas XXIII, XXIV, XXV or XXVI

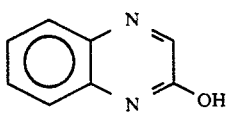
Formula XXIII

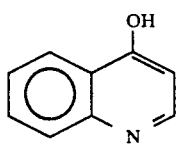
Formula XXIV

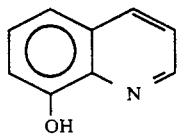
Formula XXV

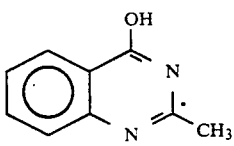
Formula XXVI

These heterocyclic ring compounds can, if desired contain inert ring substituents such as, for example, aliphatic or aromatic hydrocarbon groups containing suitably from 1 to about 20, more suitably from 1 to about 15, most suitably from 1 to about 10 carbon atoms, or a halogen, preferably bromine.

Suitable di- or multi-unsaturated aliphatic or cycloaliphatic compounds containing organosiloxane moieties in their backbone include, for example, those represented by the following general formulas XXVII, XXVIII, XXIX or XXX

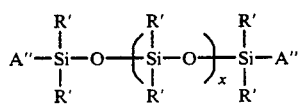
Formula XXVII

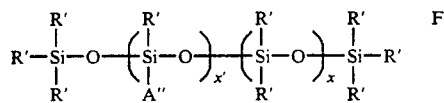
Formula XXVIII

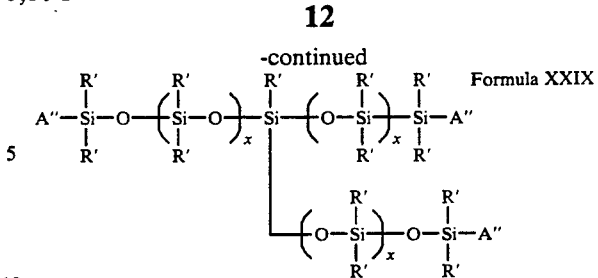
Formula XXIX

Formula XXX wherein each R', x, x' and x" is as previously defined in Formulas XIX to XXII; and each A" is an unsaturated aliphatic or unsaturated cycloaliphatic group containing suitably from 2 to about 20, more suitably from 2 to about 15, most suitably from 2 to about 10, carbon atoms. Particularly suitable A" groups include, for example,

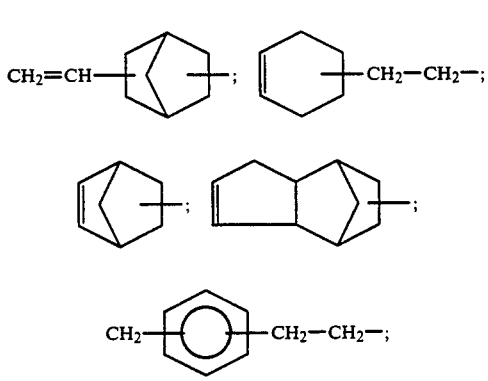

or the like.

These di- or multi-unsaturated aliphatic or di-or multi-unsaturated cycloaliphatic compounds containing organosiloxane moieties in their backbone can be prepared via hydrosilylation of corresponding unsaturated aliphatic or cycloaliphatic alkenes with corresponding hydrosiloxane compounds represented by formulas XIX, XX, XXI or XXII as described above.

Suitable di- or multi-unsaturated aliphatic or di- or multi-unsaturated cycloaliphatic compounds include, for example, those having from about 4 to about 400, preferably from about 4 to about 200 carbon atoms, such as, for example, 1,4-pentadiene, 1,4-hexadiene, 1,5-hexadiene, 1,7-octadiene, 4-methyl-1,3-pentadiene, 5-vinyl-2-norbornene; 4-vinyl-1-cyclohexene; dicyclopentadiene; 1,4-cyclohexadiene; cyclopentadiene; bicyclo-(2.2.1)-hepta-2,5-diene; pentacyclo$(8.2.1.1^{4,7}.0^{2,9}0^{3,8})$-tetradeca-5,11-diene; methylcyclopentadiene dimer; 5-ethylidene-2-norbornene; 5-methylene-2-norbornene; (−) limonene; (+) limonene; 1,5-cyclodecadiene; 1,5-cyclooctadiene; and the like.

The novel compounds of the present invention which contain aromatic cyanate groups and which also contain organosiloxane moieties include those compounds represented by the aforementioned general formulas I, II, III, or IV wherein each R' is independently a hydrocarbyl group having suitably from 1 to about 20, more suitably from 1 to about 10, most suitably from 1 to about 4, carbon atoms; each Y is a hydrocarbyl group having from 2 to about 20, preferably from about 2 to about 15, more preferably from about 2 to about 10 carbon atoms or an entity represented by the aforementioned formulas V, VI, VII, VIII, IX, X, or XI with the proviso that at least an average of more than one Y is other than a hydrocarbyl group; and each A is independently a divalent hydrocarbyl group having from 1 to about 20, preferably from about 1 to about 15, more preferably from about 1 to about 10 carbon atoms, —O—, —S—, —S—S—, —SO—, —SO$_2$—, or —CO—; each A' is independently a divalent hydrocarbyl group having from 1 to about 20, preferably from about 1 to about 10, more preferably from about 1 to about 2 carbon atoms; each Q is independently hydrogen or an alkyl group having from 1 to about 10, preferably from about 1 to about 6, more preferably from about 1 to about 4 carbon atoms; each Q' is independently a tetravalent hydrocarbyl group having from 1 to about 20, preferably from about 1 to about 10, more preferably from about 1 to about 4 carbon atoms; each R is independently hydrogen or an alkyl group having from 1 to about 3 carbon atoms; each X is independently hydrogen, a hydrocarbyl or hydrocarbyloxy group having from 1 to about 12, preferably from about 1 to about 6, more preferably from about 1 to about 4 carbon atoms, a halogen atom, or a hydroxyl group; each X' is independently hydrogen or an unsaturated aliphatic or unsaturated cycloaliphatic group or such unsaturated aliphatic or unsaturated cycloaliphatic group having an oxygen atom between such group and the aromatic ring, such as, for example, —CH$_2$—CH=CH$_2$, —CH=CH$_2$, —O—CH$_2$—CH=CH$_2$, cyclohexenyl, bicyclo-(2.2.1)hept-1-yl, vinyl benzyl ether or the like; each X" is independently a divalent aliphatic or a divalent cycloaliphatic group; each m independently has an average value from about 0.01 to about 8, preferably from about 1 to about 6, more preferably from about 2 to about 4; each m' independently has an average value from about zero to about 8, preferably from about 1 to about 6, more preferably from about 2 to about 4; each n independently has a value of zero or 1; each n' independently has an average value from about 0.001 to about 20, preferably from about 0.01 to about 12, more preferably from about 0.03 to about 5; each n$^1$ independently has a value from 1 to about 3; each p independently has a value from zero to about 10, preferably from about 1 to about 5, more preferably from about 1 to about 3; each p' independently has an average value from zero to about 8, preferably from about 1 to about 6, more preferably from about 2 to about 4; and each s, t and u independently has a value from 1 to about 3 with the proviso that the sum of s, t and u satisfies the valency of the ring; each x independently has a value from zero to about 500, preferably from about zero to about 250, more preferably from about zero to about 125; each x' independently has a value from 2 to about 500, preferably from about 2 to about 250, more preferably from about 2 to about 125; each x" independently has a value from 2 to about 10, preferably from about 2 to about 8, more preferably from about 4 to about 6; and the sum of x and x' is from about 2 to about 1000, preferably from about 2 to about 500, more preferably from about 2 to about 250.

If desired, the cyanate-containing compounds of the present invention can be blended with other cyanate-containing compounds, i.e. cyanate-containing compounds which do not contain the siloxane moieties.

Particularly suitable such cyanate-containing compounds include, for example, bisphenol A dicyanate, bisphenol K dicyanate, bisphenol F dicyanate, methylene bis (3,5-dimethylphenyl-4-cyanate), 4,4'-thiodiphenylcyanate, polycyanate of phenol-formaldehyde novolac resins, polycyanate of cresol-formaldehyde novolac resins, polycyanate of dicyclopentadiene-phenol resins, polycyanate of dicyclopentadiene-cresol resins, combinations thereof and the like.

In those compositions containing mixtures polycyanate resins (cyanate-containing compound) containing organosiloxane moieties and polycyanate resins (cyanate-containing compound) which are substantially free of organosiloxane moieties, they are employed in amounts of from about 1 to about 99, preferably from about 5 to about 90, more preferably from about 15 to about 85 percent by weight of polycyanate resin (cyanate-containing compound) containing organosiloxane moieties and from about 99 to about 1, preferably from about 95 to about 10, more preferably from about 85 to about 15 percent by weight of polycyanate resin (cyanate-containing compound) which is substantially free of organosiloxane moieties. These percentages being based upon the combined weight of polycyanate resin containing organosiloxane moieties and the polycyanate resin which is substantially free of organosiloxane moieties.

Suitable curing catalysts for the cyanate-containing compounds of the present invention include, for example, acids, bases, nitrogen or phosphorus compounds, transition metal salts or complexes, such as metal salts of aliphatic and aromatic carboxylic acids, tertiary amines, combinations thereof and the like. Particularly suitable curing agents include, for example, cobalt octoate, cobalt naphthenate, cobalt acetylacetonate (Co(AcAc)$_3$), zinc octoate, zinc naphthenate, tin octoate, diazobicyclo-(2,2,2)-octane, triethylamine, combinations thereof and the like.

These curing catalysts are employed in amounts of from about 0.0001 to about 10, preferably from about 0.001 to about 1, more preferably from about 0.01 to about 0.1 percent by weight based on total polycyanate resin.

The cyanate-containing resins and curable compositions of the present invention can be blended with other materials such as, for example, solvents or diluents, fillers, pigments, dyes, flow modifiers, thickeners, reinforcing agents, surfactants, antioxidants, surfactants, combinations thereof and the like.

The compositions of the present invention can be employed in such applications as adhesives, coatings, laminates, composites, encapsulants, filament winding, molding, and the like.

The following examples are illustrative of the invention but are not to be construed as limiting the scope thereof in any manner.

EXAMPLE 1

A. Preparation of 1,3-bis'(3'-(2-hydroxylphenyl)-propyl)-1,1,3,3-tetramethyldisiloxane To an 85 ml toluene solution of 67.1 g 2-allylphenol (0.5 mole) and 0.4 g 5% H$_2$PtCl$_6$ in t-amyl alcohol is added a 15 ml of a toluene solution of 38.8 g (0.25 mole) of 1,1,3,3-tetramethyldisiloxane at 75° C. The addition is complete in 1 hour. The mixture is then heated at 85° C. for 1 hour and 105° C. for 3 hours. After washing three times successively with 100 ml portions of H$_2$O, 101 g of the 2:1 molar adduct 1,3-bis'(3'-(2-hydroxylphenyl)-propyl)-1,1,3,3-tetramethyldisiloxane (>92% pure by GC, gas chromatography) having a brown color is obtained after stripping off solvent. The structure is confirmed by 1H NMR and IR. IR(neat): 3350(broad, aromatic hydroxyl), 1050-1100(strong, siloxane)cm$^{-1}$; 1H NMR (CDCl$_3$-TMS): 0-0.8 ppm (m, Si—CH$_3$ & Si—CH$_2$—), 1.6 ppm (m, —CH$_2$—), 2.7 ppm (t, —CH$_2$—), 5.5-5.6 ppm (broad, D$_2$O exchangeable), 6.8-7.0 ppm (m, Ar—H).

B. Preparation of 1,3-bis-(3'-(2-cyanatophenyl)-propyl)-1,1,3,3-tetramethyldisiloxane To a 750 ml methylene chloride solution containing 40.2 g (0.1 mole) of 1,3-bis-(3'-(2-hydroxylphenyl)-propyl)-1,1,3,3-tetramethyldisiloxane from A above is added 25.42 g (0.24 mole, 97% purity) of cyanogen bromide (CNBr) at −30° C. and 26.31 g (0.26 mole, 98% purity) of triethylamine is then added at −30° C. in 15 minutes. An exothermic reaction is observed. After completion of addition, the reaction temperature is maintained at −25° C. to −15° C. for 30 minutes and −15° C. to −5° C. for 30 min. The mixture is then hydrolyzed with 150 ml H$_2$O and washed once with 0.2N HCl and three times with 150 ml portions of H$_2$O. The solution is dried over MgSO$_4$, resulting in 45 g of a viscous liquid after stripping off solvent at <145° C./<10 mm Hg. The structure is confirmed by IR and 1H NMR. IR(neat): 3350 cm$^{-1}$ (aromatic hydroxyl disappeared), 2250 cm$^{-1}$ (strong —CN); 1H NMR (CDCl$_3$): 0 to 0.8 ppm (m, Si—CH$_3$ and Si—CH$_2$—), 1.6-2.0 ppm (m, —CH$_2$—), 2.8 ppm (t, —CH$_2$—), 7.3-7.6 ppm (m, Ar—H).

EXAMPLE 2

A. Preparation of 1,3-bis-(5-vinylnorbornyl)-1,1,3,3-tetramethyldisiloxane

To a 10 ml toluene solution of 60.1 g (0.5 mole) of 5-vinyl-2-norbornene and 0.30 g of 55 H$_2$PtCl$_6$ in t-amyl alcohol is added 29.6 g of 1,1,3,3-tetramethyl-disiloxane (0.22 mole, 90% purity) at 45° C. to 50° C. for 1 hour and 30 minutes. The reaction is complete after keeping the reaction at 55° C. to 60° C. for 6 hours. The mixture is then dissolved in 250 ml of methyl ethyl ketone. After washing successively with 100 ml portions of water four times, 65 g of 1,1-bis-(-5-vinylnorbornyl)-1,1,3,3-tetramethyldisiloxane is obtained after stripping off solvent at 120° C./110 mm Hg. The structure of the product is confirmed by IR and 1H NMR as follows: IR(neat): 1050-1150 cm$^{-1}$ (strong, —Si—O—), Si—H bond absorption peak at 2150 cm$^{-1}$ disappeared. 1H NMR (CDCl$_3$-TMS): 0 to 0.7 ppm (m, Si—CH$_3$ and Si—CH$_2$—); 1.0-2.7 ppm (m, aliphatic and cycloaliphatic C—H); 4.8-5.2 ppm (m, alkene C—H) and 5.5-6.2 ppm (m, Alkene C—H).

B. Preparation of 1,3-bis-(-5-(2',4'-dihydroxyphenylethyl)-norbornyl)-1,1,3,3-tetramethyldisiloxane To an 80 ml chlorobenzene solution of 22 g resorcinol (0.2 mole), and 0.38 g of methylsulfonic acid is added a 15 ml of a chlorobenzene solution of 37.4 g (0.1 mole) of 1,3-bis-(5-vinylnorbornyl)-1,1,3,3-tetramethyldisiloxane at 100° C. in 25 minutes. The mixture is reacted at 100° C. to 105° C. for 3 hours. After hydrolysis, the solution is washed three times with 100 ml portions of H$_2$O. 54 g of a viscous semi-solid having brown color is obtained after stripping off solvent at 140° C./<10 mm Hg. IR (neat): 3400(broad, aromatic hydroxyl), 1050(strong, siloxane)cm$^{-1}$; 1H NMR (CDCl$_3$): 0 to 0.7 ppm (m, Si—CH$_3$ & Si—CH=), 1.0-3.0 ppm (m, cycloaliphatic C—H), 5.8-6.0 ppm (D$_2$O exchangeable), 6.5-7.3 ppm (m, Ar—H).

C. Preparation of 1,3-bis-(5-(2',4'-dicyanatophenylethyl)-norbornyl)-1,1,3,3-tetramethyldisiloxane To a 700 ml methylene chloride solution containing 49 g (0.085 mole) of 1,3-bis-(5-(2',4'-dihydroxyphenylethyl)-norbornyl)-1,1,3,3-tetramethyldisiloxane is added 41.16 g (0.377 mole) of cyanogen bromide, CNBr, at −30° C. and after the addition of CNBr, 40.75 g of triethylamine (0.373 mole, 98% purity) is then added at −20° C. in 10 minutes. The reaction is carefully monitored in order to control reaction temperature at −20° C. by means of a cooling bath of glycol-dry ice. An exothermic reaction is observed and the reaction occasionally reaches a temperature of −10° C. After completion of addition, the mixture is at stirred at −20° C. to −25° C. for 30 minutes and raised to −10° C. in another 30 minutes. The mixture is then hydrolyzed with 120 ml of H$_2$O and washed once with 120 ml of 0.2N HCl and three times with 120 ml portions of H$_2$O. The solution is then dried over MgSO$_4$ and 54 g of a very viscous resin is obtained after stripping off solvent at <170° C./10 mm Hg.

The structure is confirmed by IR and 1H NMR: IR(neat):3300 cm$^{-1}$(broad aromatic hydroxyl groups absorption peak disappeared), 2300 cm$^{-1}$(strong —CN absorption peak); 1H NMR (CDCl$_3$-TMS): 0.7-0.9 ppm (m, Si—CH$_3$ and Si—CH$_2$); 1.5-3.0 (m, aliphatic and cycloaliphatic C—H); 7.0-8.0 ppm (m, aromatic C—H).

EXAMPLE 3

A. Reactivity

The reactivity of uncured cyanate esters (Examples 1B and 2C) is measured by differential scanning calorimetry (DSC) method using a DuPont series 2100 thermal analysis system with DSC model #912. A 30% Cobalt(III) acetylacetonate, [Co(AcAc)$_3$], in divinylbenzene is used as a catalyst. The concentration of Co$^{+++}$ is at about 250 ppm of the pure resin. the results are given in the following Table I.

TABLE I

|  | Sample | | |
|---|---|---|---|
|  | A | B | C |
| Resin, type, g | Ex. 1B | Ex. 1B | Ex. 2C |
|  | 10 | 10 | 10 |
| Co(AcAc)$_3$, ppm Co$^{+3}$ | None | 250 | 250 |
| Initial Exotherm Temp., °C. | 265 | 194 | 201 |
| Maximum Exotherm Temp., °C. | 302 | 250 | 270 |

B. Thermogravametric Analysis of Cured Resin

The adduct prepared in Examples 1B and 2C, optionally blended with a 2.2 functional dicyclopentadiene-phenol cyanate ester resin (DCPDCR) having a cyanate equivalent weight of 213 are blended with a catalyst Co(III) acetylacetonate (Co(AcAc)$_3$), 250 ppm Co$^{+++}$ content, and cured at 175° C. for 2 hours+220°

C. for 2 hours+245° C. for 2 hours. The results are given in the following Table II.

TABLE II

|  | Sample No. | | |
|---|---|---|---|
|  | A | B | C |
| Cyanate Ester | | | |
| type | Ex. 1B | Ex. 1B | Ex. 2C |
| pbw[a] | 100 | 30 | 100 |
| DCPDCR, pbw | None | 70 | None |
| Co(AcAc)$_3$, ppm Co$^{+3}$ | 250 | 250 | 250 |
| TGA[b], 5% weight loss, °C. | 366 | 351 | 414 |

[a]Parts by weight.
[b]Thermogravimetric Analysis.

EXAMPLE 4

The composition and properties of cyanate esters with styrene terminated organosiloxane compound

A. Synthesis of 1,3-bis-($\beta$-(4'-, or 3'-vinylphenyl)-ethyl)-1,1,3,3-tetramethyldisiloxane and its copolymer with aromatic cyanate esters To a 15 ml toluene solution of 26 g (0.2 mole) of divinylbenzene (a mixture of isomers) and 0.15 g of 5% H$_2$PtCl$_6$ in t-amyl alcohol, is added 14.89 g of 1,1,3,3-tetramethyldisiloxane at 35°–40° C. over a period of 15 minutes, then reacted at 45° C. TO 50° C. for 6 hours. The solution is washed three times with 15 ml portions of water. 27 g of a light colored 2:1 molar liquid adduct, 1,3-bis-($\beta$-(4', or 3'-vinylphenyl)-ethyl)-1,1,3,3-tetramethyldisiloxane, is obtained. The adduct is thermally reactive and can be used as a reactive diluent for aromatic cyanate esters. The uncured compound 4A has a maximum exotherm temperature of 212° C. when heated, as measured by DSC (differential scanning calorimetry method) by using a DuPont 2100 series thermal analysis system with DSC model #912.

B. Thermal Analyses of the copolymer of example 4A cured with a 2.2 functional dicyclopentadiene-phenol cyanate ester The adduct prepared in Example 4A and 2.2 functional dicyclopentadiene-phenol cyanate ester resin (DCPDCR) having a cyanate equivalent weight of 213 are blended with Co(III)acetylacetonate (Co(AcAc)$_3$) catalyst, 250 ppm Co$^{+++}$ content, and cured at 175° C. for 2 hours+220° C. for 2 hours+245° C. for 2 hours. The results are given in the following Table III.

TABLE III

|  | Sample No. | | |
|---|---|---|---|
|  | A | B | C |
| Ex. 4-A, g | None | 2 | 3 |
| DCPDCR, g | 10 | 10 | 10 |
| Co(AcAc)$_3$, g | 0.005 | 0.005 | 0.005 |
| Tg (by DSC)[a], °C. | 271 | 258 | 254 |
| (by TMA)[b], °C. | 240 | 220 | 216 |
| TGA[c], onset of weight loss, °C. | 421 | 426 | 412 |

[a]Differential Scanning Calorimetry.
[b]Thermomechanical Analysis.
[c]Thermogravimetric Analysis.

EXAMPLE 5

A. Preparation of aromatic hydroxyl-containing oligomer with organodimethyl siloxane moiety To a 100 ml toluene solution of 100 g hydromethylsiloxane-dimethylsiloxane copolymer terminated with trimethylsiloxyl groups; (15% hydromethylsiloxane content; 5.63 eq. Si-H/mole, M.W. 2250) is added 20 ml toluene solution containing 20.13 g (0.15 mole) of 2-allylphenol and 0.25 g of 5% solution of H$_2$PtCl$_6$ in t-amyl alcohol at 85° C. for 1 hour. The clear solution is then heated at 90° C. to 95° C. for 4 to 6 hours. 20.2 g (0.25 mole) of norborlyene is then added at 60° C. to 65° C. in 20 minutes and heated for 4 to 6 hours. The mixture is then dissolved in 150 ml methyl ethyl ketone and the solution is washed successively four times with 100 ml portions of water. The organic layer is collected and 125 g of viscous liquid (3.5 eq. of aromatic hydroxyl/mole) is obtained after stripping off the solvents and excessive norborlyene at 130° C./15 mm Hg. The structure of the product is confirmed by 1H NMR and IR as follows: IR(neat): 3450$^{cm-1}$ (broad, aromatic hydroxyl), 1000–1100$^{cm-1}$ (strong, siloxane). Si—H bond absorption peak at 2100–2200$^{cm-1}$ disappeared in IR. 1H NMR(CDCl$_3$-TMS): 0.4–0.6 ppm (m, Si—CH$_3$ and Si—CH$_2$—), 1.0–2.4 ppm (m, aliphatic and cycloaliphatic C—H), 3.0 ppm(t, Ar—CH$_2$—), 5.6 ppm(broad, Ar—OH, D$_2$O exchangeable), 7.1–7.5 ppm (m, Ar—H).

B. Preparation of aromatic cyanate ester containing oligomer with organodimethylsiloxane moiety To a 400 ml methylene chloride solution containing 129.5 g product from A above (3.5 aromatic hydroxyl/mole) is added 21.84 g (0.20 mole, 97% purity) of cyanogen bromide (CNBr) at −30° C., and 22.72 g (0.22 mole, 98% purity) of triethyl amine is then added dropwise at −30° C. in 15 min. An exothermic reaction is observed and the temperature is controlled not to exceed above −15° C. by means of a cooling bath of glycol-dry-ice. After completion of addition, the reaction temperature is maintained at −25° C. to −15° C. for 30 minutes and −15° C. to −10° C. for another 30 minutes. The mixture is then hydrolyzed with 100 ml H$_2$O, washed once with 0.2N HCl and followed by washing four times with 120 ml portions of H$_2$O. The solution is then dried over MgSO$_4$, resulting in 132 g of a viscous liquid (3.5 eq. of aromatic —OCN/mole) after stripping off solvent at <140° C./5 mm Hg. The structure is confirmed by IR and 1H NMR, IR(neat): 3450$^{cm-1}$(aromatic hydroxyl disappeared), 2250$^{cm-1}$(strong —CN); 1H NMR(CDCl$_3$-TMS):0.2–0.6 ppm (m, Si—CH$_3$, and Si—CH$_2$), 1.0–2.5 ppm (m, —CH$_2$—), 2.8 ppm (t, Ar—CH$_2$—), 7.0–7.5 ppm (Ar—H).

EXAMPLE 6

A. Preparation of aromatic hydroxyl-containing compounds with organodimethylsiloxane moiety To a 100 ml toluene solution of 100 g hydromethyl-siloxane-dimethylsiloxane copolymer (trimethylsiloxy terminated; 30% hydromethylsiloxy content: 10.25 eq. Si—H/mole; M.W. 2050) is added a 20 ml toluene solution containing 33.54 g of 2-allylphenol (0.25 mole) and 0.25 g 5% H$_2$PtCl$_6$ in t-amyl alcohol at 85° C. for 1 hour. The clear solution is then heated at 85° C. to 90° C. for 6 to 8 hours and 40.1 g of norborylene (0.50 mole) is then added at 60° C. to 65° C. in 30 minutes and heated for 2 to 4 hours. The mixture is dissolved in 150 ml methyl ethyl ketone and the solution is washed successively four times with 100 ml portions of H$_2$O. The organic layer is collected and 142 g of viscous liquid (5.0 eq. of aromatic hydroxyl/mole) is obtained after stripping off the solvents and excessive norborylene at 130° C./15 mm Hg. The structure is confirmed by 1H NMR and IR: IR (neat): $3450^{cm-1}$(broad, aromatic hydroxyl), $1000-1100^{cm-1}$ (strong, siloxane). Si—H bond absorption peak at $2100-2200^{cm-1}$ disappeared in IR. 1H NMR (CDCl$_3$-TMS): 0.4–0.6 ppm (m, Si—CH$_3$ and Si—CH$_2$—), 1.0–2.4 ppm (m, aliphatic and cycloaliphatic C—H), 3.0 ppm (t, Ar—CH$_2$), 5.7 ppm (broad, Ar—OH, D$_2$O exchangeable), 7.0–7.5 ppm (m, Ar—H).

B. Preparation of aromatic cyanate ester containing oligomer with organodimethylsiloxane moiety To a 400 ml methylene chloride solution containing 125.5 g of product from A above (5.0 aromatic hydroxyl/mole) is added 28.4 g (0.26 mole, 97% purity) of cyanogen bromide (CNBr) at −30° C., and 28.92 g (0.28 mole, 98% purity) of triethyl amine is then added dropwise at −30° C. in 15 minutes. An exothermic reaction is observed and the addition temperature is controlled not to exceed above −10° C. by means of a cooling bath of glycol-dry ice. After completion of addition, the reaction temperature is maintained at −25° C. to −15° C. for 30 minutes and −15° C. to −10° C. for another 30 minutes. The mixture is then hydrolyzed with 100 ml H$_2$O, washed with 0.2N HCl, followed by washing four times with 120 ml portions of water. The solution is dried over MgSO$_4$, resulting in 120 g of a viscous liquid (5.0 eq. of aromatic —OCN/mole) after stripping off solvent at 140° C./5 mm Hg. The structure is confirmed by IR and 1H NMR, IR (neat): $3450-3500^{cm-1}$ (aromatic hydroxyl disappeared, $2250-2300^{cm-1}$ (strong, —CN ester); 1H NMR (CDCl$_3$-TMS): 0.2–0.6 ppm (m, Si—CH$_3$, Si—CH$_2$), 0.8–2.5 ppm (m, —CH$_2$—), 2.8 ppm (t, Ar—CH$_2$—), 7.0–7.5 (m, Ar—H).

EXAMPLE 7

A. Preparation of aromatic hydroxyl-containing compounds with organodimethylsiloxane moiety To a 150 ml toluene solution of 200 g hydromethylsiloxane-dimethylsiloxane copolymer (trimetylsiloxy terminated; 30% hydromethylsiloxy content: 10.25 eq. Si—H/mole; M.W. 2050) is added a 50 ml toluene solution containing 87.19 g 2-allylphenol (0.65 mole) and 0.7 g 5% H$_2$PtCl$_6$ in t-amyl alcohol at 85° C. for 1 hour. The clear solution is then heated at 85° C. to 90° C. for 6 to 8 hours. 65.91 g norborlyene (0.70 mole) is then added at 60° C. to 65° C. in 30 minutes and stirred at this temperature for another 4 to 6 hours. The mixture is then dissolved into 150 ml of methyl ethyl ketone and washed successively four times with 100 ml of water each time. The organic layer is collected and 265 g of viscous liquid (6.5 eq. of aromatic hydroxyl/mole) is obtained after stripping off the solvents and excessive norborlyene at 130° C./15 mm Hg. The structure is confirmed by IR and 1H NMR: IR (neat): $3450-3500^{cm-1}$ (broad, aromatic hydroxyl), $1000-1100^{cm-1}$ (strong, siloxane). Si—H bond absorption peak at $2100-2200^{cm-1}$ disappeared. 1H NMR (CDCl$_3$-TMS): 0.4–0.6 ppm (m, Si—CH$_3$ and Si—CH$_2$), 1.0–2.4 ppm (m, aliphatic and cycloaliphatic C—H), 3.0 ppm (t, Ar—CH$_2$), 5.8–6.0 ppm (broad, Ar—OH, D$_2$O exchangeable), 7.0–7.5 ppm (m, Ar—H).

B. Preparation of aromatic cyanate ester containing organodimethylsiloxane moiety To a 400 ml methylene chloride solution containing 99 g product from A above (6.5 aromatic hydroxyl/mole) is added 28.40 g (0.26 mole, 97% purity) of cyanogen bromide (CNBr) at −30° C., and 29.9 g (0.28 mole, 98% purity) of triethyl amine is then added dropwise at −30° C. in 15 minutes. An exothermic reaction is observed and the temperature is controlled not to exceed above −10° C. by means of a cooling bath of glycol/dry-ice. After completion of addition, the reaction is maintained at −25° C. to −15° C. for 30 minutes and followed at −15° C. to −10° C. for another 30 minutes. The mixture is then hydrolyzed by 100 ml of H$_2$O and washed once by 0.2N HCl. The solution is then washed successively four times with 120 ml portions water. The clear solution is dried over MgSO$_4$, resulting in 105 g of a viscous liquid (6.5 eq. of aromatic —OCN/mole) after stripping off solvent at 140° C./5 mm Hg. the structure of the product is confirmed by IR and 1H NMR. IR (neat): $3450^{cm-1}$ (aromatic hydroxyl disappeared), $2270-2280^{cm-}$(strong, aromatic —OCN). 1H NMR (CDCl$_3$-TMS): 0.2–0.6 ppm (m, Si—CH$_3$ and Si—CH$_2$—), 0.7–2.6 ppm (m, aliphatic and cycloaliphatic CH). 2.8(t, Ar—Ch$_2$—), 6.8–7.3 ppm (m, Ar—H).

EXAMPLE 8

Morphology and thermal mechanical properties of the polymer blend of examples 1b, 5b, 6b and 7b with 2.2 functional dicyclopentadiene-phenol cyanate ester (DCPDCR) having a functionality of 2.2 and an equivalent weight of 213. The blends are cured at 175° C. for 1 hour plus 210° C. for 1.5 hours and finally at 250° C. for 2 hours. The results are given in Table III.

TABLE III

| | Sample No. | | | | | | |
|---|---|---|---|---|---|---|---|
| | A | B | C | D | E | F | G |
| Cyanate Ester | | | | | | | |
| type | 1b | 5b | 6b | 7b | 7b/1b | 7b | 7b/1b |
| pbw[a] | 1.0 | 1.0 | 1.0 | 1.0 | 0.8/0.2 | 1.5 | 1.0/0.5 |
| DCPDCR, pbw | 9.0 | 9.0 | 9.0 | 9.0 | 9.0 | 8.5 | 8.5 |
| Co(AcAc)$_3$, ppm Co$^{+3}$ | 250 | 250 | 250 | 250 | 250 | 250 | 250 |
| Compatibility[b] | E | P | G | G | G-E | G | G-E |
| Tg (DSC)[c], °C. | 243 | — | 265 | 264 | 259 | 263 | 250 |
| Phases | one | two | two | two | two | two | two |

[a]Parts by weight.
[b]Compability of DCPDCR with cyanate ester resins 1b, 5b, and 7b.
E = excellent; G = good and P = poor.
[c]Differencial Scanning Calorimetry.

What is claimed is:

1. A blend comprising (1) from about 1 to about 99 percent by weight based upon the combined weight of components (1) and (2) of at least one compound containing an average of more than one cyanate group and at least one organosiloxane moiety per molecule; and (2) from about 99 to about 1 percent by weight based upon the combined weight of components (1) and (2) of at least one compound containing an average of more than one cyanate group per molecule which is substantially free of organosiloxane moieties.

2. A blend of claim 1 wherein component (1) is a compound represented by the following general formulas I, II, III, or IV Formula I

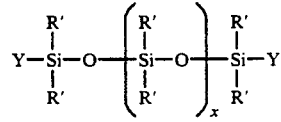

-continued

Formula II

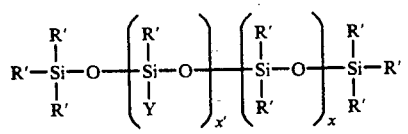

Formula III

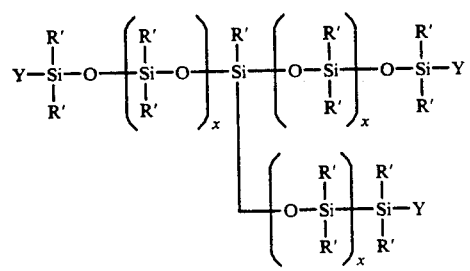

Formula IV

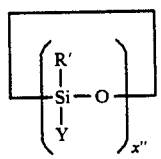

wherein each R' is independently a hydrocarbyl group having from 1 to about 20 carbon atoms; each Y is a hydrocarbyl group having from 2 to about 20 carbon atoms or an entity represented by the following formulas V, VI, VII, VIII, IX, X, or XI with the proviso that at least an average of more than one Y is other than a hydrocarbyl group:

Formula V

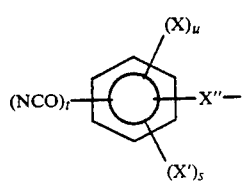

Formula VI

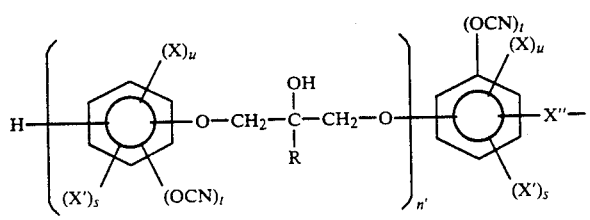

Formula VII

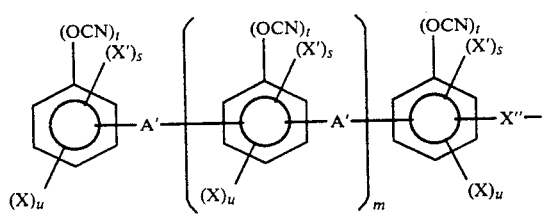

Formula VIII

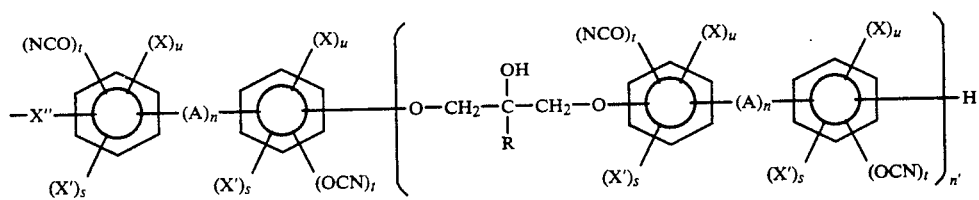

Formula IX

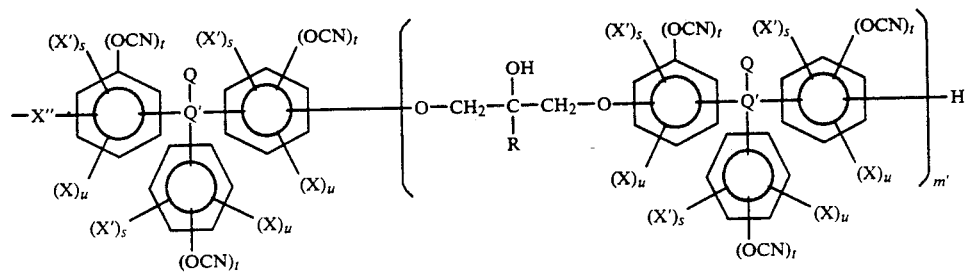

-continued

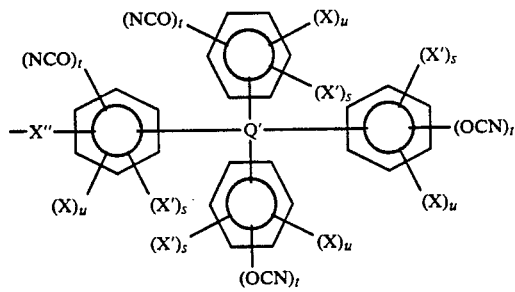

Formula X

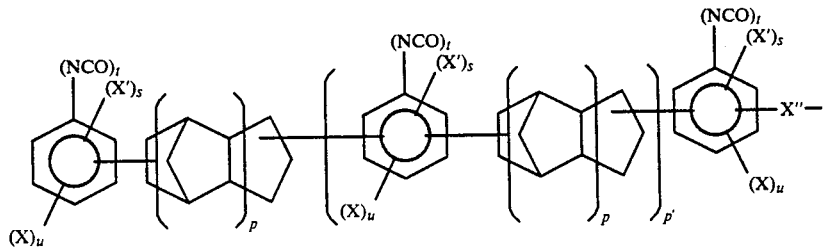

Formula XI wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom, or a hydroxyl group; each X' is independently hydrogen or an unsaturated aliphatic or unsaturated cycloaliphatic group or such unsaturated aliphatic or unsaturated cycloaliphatic group having an oxygen atom between such group and the aromatic ring; each X" is independently a divalent aliphatic or a divalent cycloaliphatic group; each m independently has an average value from about 0.01 to about 8; each m' independently has an average value from about zero to about 8; each n independently has a value of zero or 1; each n' independently has an average from about 0.001 to about 20; each n$^1$ independently has a value from 1 to about 3; each p independently has a value from zero to about 10; each p' independently has an average value from zero to about 8; and each s, t and u independently has a value from 1 to about 3 with the proviso that the sum of s, t and u satisfies the valency of the ring; each x independently has a value from zero to about 500; each x' independently has a value from 2 to about 500; each x" independently has a value from 2 to about 10; and the sum of x and x' is from about 2 to about 1000.

3. A blend of claim 2 wherein in component (1) each R' is independently a hydrocarbyl group having from 1 to about 20 carbon atoms; each A is independently a divalent hydrocarbyl group having from 1 to about 15 carbon atoms, —O—, —S—, —S—S—, —SO—, —SO$_2$—, or —CO—; each A' is independently a divalent hydrocarbyl group having from 1 to about 10 carbon atoms; each Q is independently an alkyl group having from 1 to about 6 carbon atoms; each Q' is independently a tetravalent hydrocarbyl group having from 1 to about 10 carbon atoms; each R is hydrogen; each X is independently hydrogen, a hydrocarbyl or hydrocarbyloxy group having from 1 to about 6 carbon atoms, bromine or a hydroxyl group; each X' is independently —CH$_2$—CH=CH$_2$, —CH=CH$_2$, —O—CH$_2$—CH=CH$_2$, cyclohexenyl, bicyiclo-(2.2.1)hept-1-yl, vinyl benzyl ether; each X" is independently, —CH$_2$—CH$_2$—CH$_2$—, —CH$_2$—CH$_2$—, —O—CH$_2$—CH$_2$—CH$_2$—,

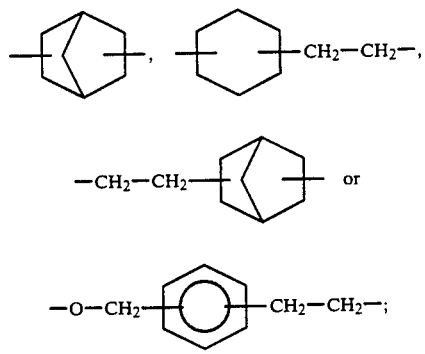

each m independently has an average value from about 1 to about 6; each m' independently has an average value from about 1 to about 6; each n has a value of 1; each n' independently has an average value from about 0.01 to about 12; each n$^1$ independently has a value from 1 to about 3; each p independently has a value from about 1 to about 5; each p' independently has an average value from about 1 to about 6; each t independently has a value of 1; each x independently has a value from zero to about 250; each x' independently has a value from 2 to about 250; x" has a value from about 2 to about 8; and the sum of x and x' is from about 2 to about 500.

4. A blend of claim 3 wherein in component (1) each R' is independently a hydrocarbyl group having from 1 to about 10 carbon atoms; each A is independently a divalent hydrocarbyl group having from 1 to about 10 carbon atoms, —O—, —S—, —S—S—, —SO—, —SO$_2$—, or —CO—; each A' is independently a divalent hydrocarbyl group having from 1 to about 2 carbon atoms; each Q' is independently a tetravalent hydrocarbyl group having from 1 to about 4 carbon atoms; each X is independently hydrogen, a hydrocarbyl or hydrocarbyloxy group having from 1 to about 4 carbon atoms, bromine or a hydroxyl group; each m independently has an average value from about 2 to about 4; each m' independently has an average value from about 2 to about 4; each n' independently has an average value from about 0.03 to about 5; each $n^1$ independently has a value of 1; each p independently has a value from about 1 to about 3; each p' independently has an average value from about 2 to about 4; each x independently has a value from zero to about 125; each x' independently has a value from 2 to about 125; x" has a value from about 4 to about 6; and the sum of x and x' is from about 2 to about 250.

5. A blend of claim 3 wherein component (1) is a compound selected from the group consisting of
(a) a compound represented by Formula I wherein each R' is a methyl group and x has a value of zero, Y is represented by formula VI wherein each X is hydrogen or methoxy group, X" is —CH₂—CH₂—CH₂—, and each s and t has a value of 1;
(b) a compound represented by Formula I wherein each R' is a methyl group and x has a value of zero, Y is represented by formula V wherein each X group is hydrogen or methoxy group, X" is the group

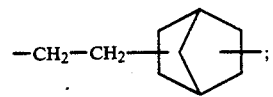

s has a value of 1; and t has a value of 2; and
(c) a compound represented by Formula II wherein, each R' is a methyl group, the sum of the average values of x and x' is from about 5 to about 40 with from about 15% to about 50% of the sum being contributed by x and from about 85% to about 50% of the sum being contributed by x', and each Y is a hydrocarbyl group having from about 4 to about 10 carbon atoms or the group represented by formula V, wherein each X and X' is hydrogen or methoxy group, X" is —CH₂—CH₂—CH₂—, s and t each has a value of 1; and the compound contains an average of from about 2 to about 30 cyanate ester groups per molecule.

* * * * *